United States Patent [19]

McCulloch et al.

[11] Patent Number: 4,878,841

[45] Date of Patent: Nov. 7, 1989

[54] PERIODONTAL PROBE

[76] Inventors: Christopher A. G. McCulloch, 9 Holloway Road, Islington, Ontario, Canada, M9A 1E7; Peter Birek, 169 Hillcrest Ave., Willowdale, Ontario, Canada, M2N 3N9

[21] Appl. No.: 876,115

[22] Filed: Jun. 19, 1986

[51] Int. Cl.[4] .............................................. A61C 19/04
[52] U.S. Cl. ..................................... 433/72; 433/120; 433/215; 128/776
[58] Field of Search ................... 433/33, 72, 120, 215; 128/776, 777

[56] References Cited

U.S. PATENT DOCUMENTS

| 381,844 | 4/1888 | Morse | 433/20 |
| 3,943,914 | 3/1976 | Grenfell et al. | 128/776 |
| 4,250,895 | 2/1981 | Lee | 128/776 |

OTHER PUBLICATIONS

Van Der Velden, U. and J. H. De Vries, "Introduction of a New Peridontal Probe: The Pressure Probe", Journal of Clinical Periodontology, 1978: 5: 188-197.

Primary Examiner—John J. Wilson
Assistant Examiner—Adriene J. Lepiane

[57] ABSTRACT

A method and apparatus for determining the attachment point of tissue to a tooth are provided. The apparatus comprises a body for insertion into the mouth which includes a datum surface for engagement with a location on a tooth. A probe is also provided on the body, which is moveable relative to the datum surface by way of a motor operable to control the movement of the probe in order to engage the probe with the tissue. A measuring device is also provided to measure the movement of the probe relative to the datum surface and an attitude sensing device is included to inhibit the operation of the measuring means upon movement of the body from a predetermined attitude. Furthermore, the motor includes a force control device to regulate the force applied to the probe so that the force is maintained at a predetermined value.

21 Claims, 2 Drawing Sheets

PERIODONTAL PROBE

BACKGROUND OF THE INVENTION

The present invention relates to periodontal probes and in particular to such probes useful for determining the attachment point of tissue to a tooth.

The investigation of gum disease is becoming increasingly important in dental care. The monitoring of the disease and a quantitative assessment of the effect of treatment on the disease has, however, been difficult to accomplish in an objective manner. One existing technique is to measure the depth of the pocket that forms between a tooth and the gum and to monitor variations in that pocket depth as an indication of the effectiveness of the treatment. However, the depth of the pocket may not be particularly significant as it can vary with changes in the inflammation of the gum tissue. What does however appear to be significant is determining the location of the attachment point to the tooth and any changes in this attachment point.

Previous attempts to measure accurately the attachment point of the tooth have utilised a manual probe. Direct measurement to a reference datum on the tooth with a manual probe has not been possible because a probe having an overall length in the order of 30 mm would be required. This, however, would not be manoeuvrable in the mouth of a patient. Accordingly, the manual monitoring process used to date requires a stent to be made with a reference datum marked on the stent. It is then possible to measure the distance from the datum on the stent to the point of attachment with a manual probe that need only be in the order of 12 mm long. The provision of a stent is, however, time-consuming and of course relatively expensive but more significantly the measuring technique appears to be open to error. Firstly, the reading of the calibration marks on the probe against the datum mark is open to error and there is inevitably a tendency to vary the force exerted on the manual probe so that the degree of penetration of the tip of the probe into the gum tissue will vary. This will inevitably introduce inaccuracies in the measuring technique.

It has been proposed to overcome some of these disadvantages by using an automated retractable probe that is advanced to the bottom of the pocket and then retracts, seeking to detect the surface irregularities caused by the cemento/enamel junction. The amount of retraction is then used as an indication of the attachment point of the pocket. However, in practice the detection of the cemento/enamel junction may be obscured by other background noise and it would not appear that there has been any attempt to overcome the problem of accurately and repeatedly determining the bottom of the pocket.

According to the present invention there is provided an apparatus for determining the attachment point of tissue to a tooth comprising:

a body for insertion into the mouth;

a datum surface on said body for engagement with a location on the tooth;

a probe moveable relative to said datum surface into engagement with said tissue;

drive means operable upon said probe to control movement thereof;

measuring means to measure movement of said probe relative to said datum surface, said drive means including force control means to regulate the force applied by said drive means to said probe to maintain said force at a predetermined value; and attitude sensing means located on said body for inhibiting operation of said measuring means upon movement of said body from predetermined a attitude, thereby permitting movement of said probe when said body is positioned in any attitude whilst inhibiting the measuring of such movement of said probe until said body is positioned in said predetermined attitude while allowing the measuring of movement once said body is positioned in said predetermined attitude.

By providing a constant force for the advancement of the probe, the bottom of the pocket will be repeatedly determined giving consistent measurements.

Furthermore, the provision of the attitude sensing device avoids inaccuracies in measurements due to misalignment of the probe relative to the tooth.

It is further preferred that the drive is remote from the body of the probe so that the dimensions of the probe are maintained at a minimum.

BRIEF DESCRIPTION OF THE DRAWING

An embodiment of the invention will now be described by way of example only with reference to the accompanying drawings in which.

DESCRIPTION OF A PREFERRED EMBODIMENT

Figure 1:
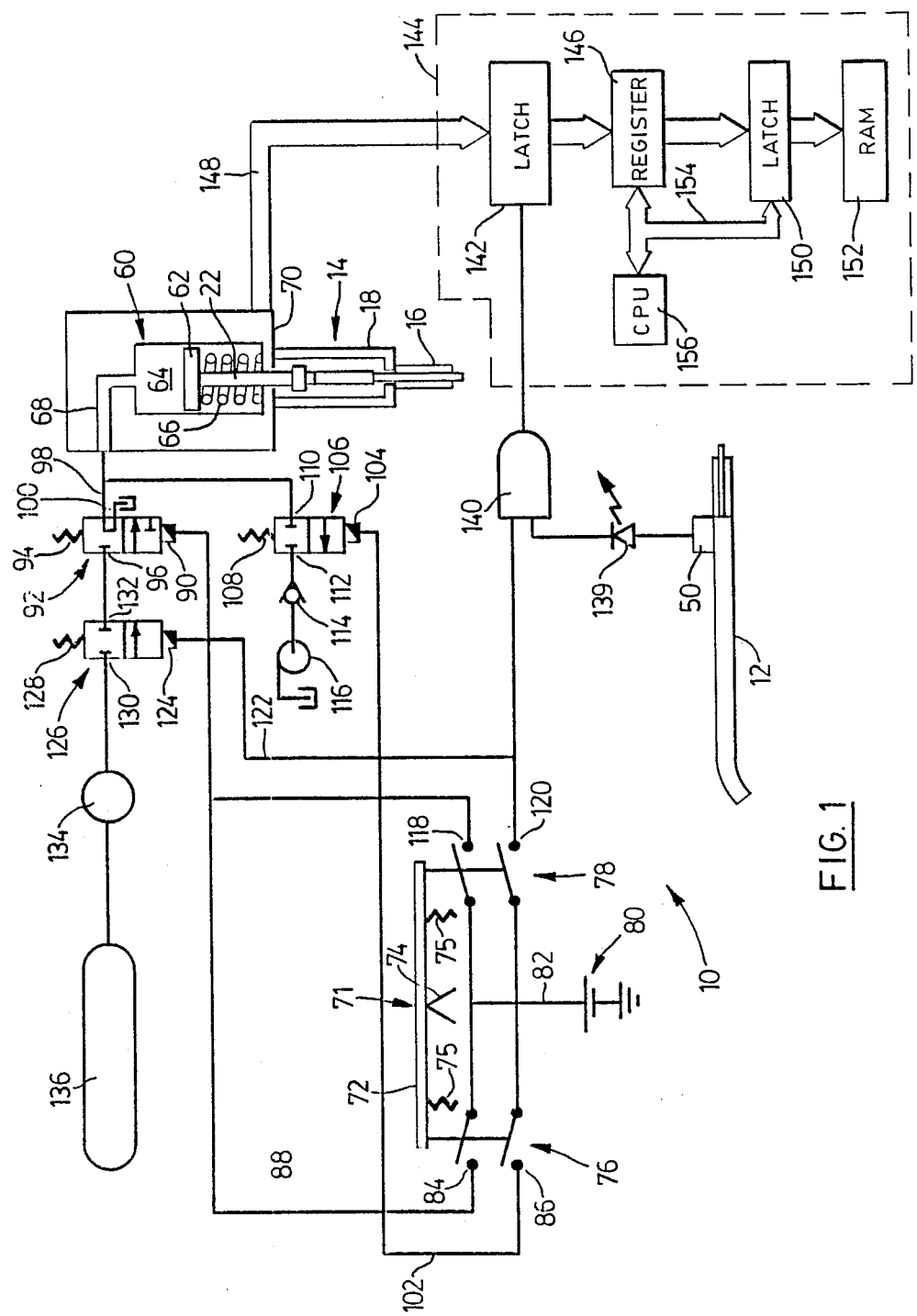
FIG. 1 is a general schematic view of a probe and associated control circuitry.

Referring to FIG. 1, a periodontal probe assembly 10 comprises a probe unit 12 and a drive and measuring unit 14. The probe unit 12 and drive and measuring unit 14 are interconnected by a flexible coaxial cable 16 connected to the drive and measuring unit 14 by a collar assembly 18. The drive and measuring unit 14 is a commercially available measuring unit known as the Heidenhain NMT30P available from Fisher Novatech, Mississauga, Ontario.

Figure 2:
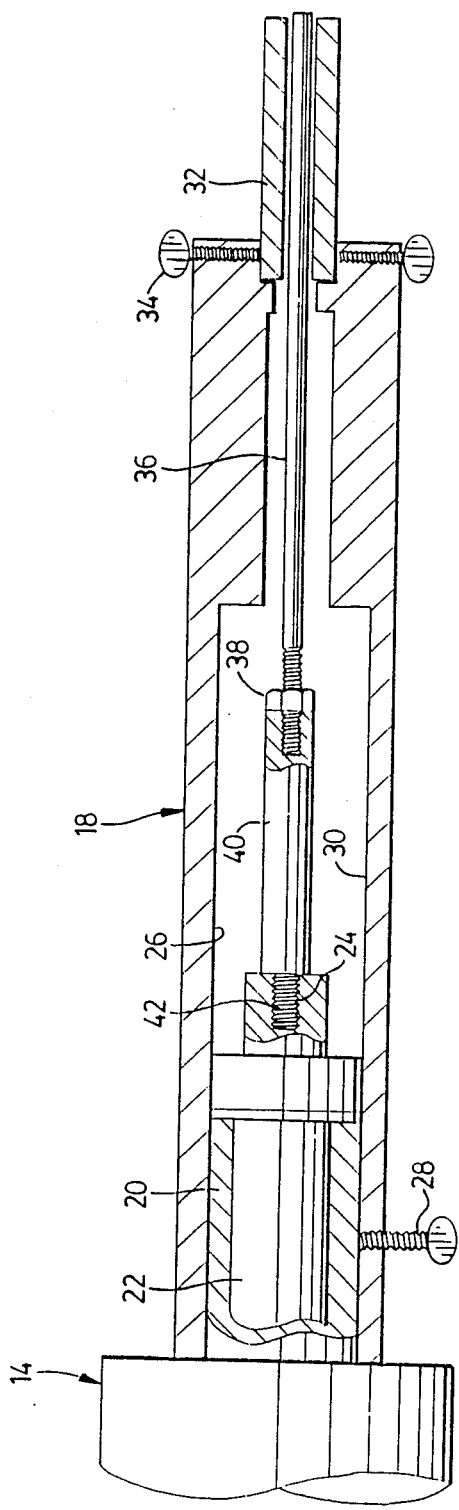
FIG. 2 is an enlarged view of a portion of the probe shown in FIG. 1.
Figure 3:
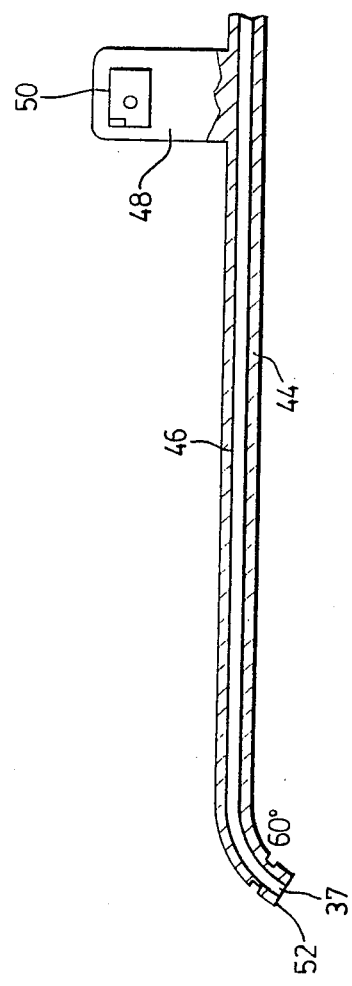
FIG. 3 is an enlarged view of a further portion of the probe shown in FIG. 1.

As can best be seen in FIG. 2, the unit 14 has a cylindrical projection 20 at its lower end in which slides a piston rod 22. The outer end of the piston rod 22 is bored and threaded as indicated at 24.

The collar assembly 18 comprises a cylindrical sleeve 26 that slides snugly over the projection 20 and is secured by a thumbscrew 28. The sleeve 26 is counterbored as indicated at 30 to allow movement of the piston rod 22 along the interior of the sleeve 26.

The sleeve 26 is also bored at its opposite end to receive the outer sheath 32 of the flexible cable 16. The sheath 32 is secured to the sleeve 26 by the pair of diametrically opposed thumbscrews 34 that engage with and grip the sheath 32. The sheath 32 slidably supports an inner cable 36 that projects within the sleeve 26 to be attached by a locking nut 38 to a connector 40 that has a threaded stud 42 projecting from one end. The stud 42 is received within the threaded bore 24 to connect the inner cable 36 to the piston rod 22 of the unit 14.

The opposite end of the outer sleeve 32 is secured to a body 44 of the probe unit 12. The body 44 is formed as an elongate tubular member having a central bore 46 to receive the extremity of inner cable 36 which constitutes the probe 37. Adjacent the end of the sheath 32, the body 44 is formed with a flat tang 48 on which is mounted a mercury switch assembly indicated at 50. The switch assembly 50 is operative to monitor the attitude of the body 44 relative to two mutually perpendicular axes.

The opposite end of the body 44 to tang 48 is curved through 60° and terminates in a planar end face 52.

The outer sheath 32 of cable 16 is polyethylene with a teflon coated inner surface and the inner cable 36 is a nickel titanium alloy (Nitenal, Unitek, Toronto) wire having a diameter of 0.50 mm. It is necessary, however, that the combination of outer sheath and inner cable reproduce measurements to the required degree of accuracy. (0.30 mm. difference between duplicate measurements.)

The drive unit 14 incorporates a pneumatic motor as indicated schematically in FIG. 1 by reference number 60. The motor 60 includes a piston 62 connected to one end of the piston rod 22 and slidable within a cylinder 64. The cylinder 64 also incorporates a counterbalancing spring 66 mounted on the piston rod 22 and acting between the end of the cylinder 64 and the piston rod 62. Fluid (Air) under pressure is supplied to the interior of the motor 60 through a supply port 68.

The unit 14 also incorporates a digital length gauge responsive to movement of the piston rod to provide a data output at data port 70 indicative of movement of the piston rod from a datum. As the unit 14 is a commercially available unit, further details of the measuring device are not believed necessary.

Control of the motor 60 is provided by a foot pedal assembly 71 including a footplate 72 mounted on a fulcrum 74. The plate 72 is biased to a horizontal position by a pair of springs 75 and can pivot in opposite directions about a transverse axis provided by the fulcrum. The footplate 72 is operably connected to two double pole switches 76, 78 that receive electrical power from a source 80 through a conductor 82.

The switch 76 includes a pair of contacts 84, 86 which are normally open when the footplate 72 is held in a horizontal position by the springs 75. Contact 84 is connected through a conductor 88 to a solenoid 90 of a solenoid operated vent valve 92. The valve 92 is biased by a spring 94 to a first position in which the inlet 96 to the valve is blocked and the outlet 98, that is connected to the supply port 68 of unit 14, is vented through a vent port 100 to atmosphere. The solenoid 90 is operable to move the valve to a position in which the inlet 96 is connected to the outlet 98 and the vent port 100 closed to allow the flow of air through the valve 92 to the supply port 68.

Contact 86 is connected through a conductor 102 to a solenoid 104 of a two-position retraction valve 106. The valve 106 is biased by a spring 108 to a first position in which an inlet port 110 teed into the supply conduit 68 is disconnected from the outlet port 112. The outlet port 112 is connected through a check valve 114 to an evacuation pump 116. The solenoid 104 operates to move the valve against the bias to spring 108 to a second position in which the inlet port 110 is connected to the outlet port 112 so that air within the supply port 68 is evacuated by the pump 116.

Switch 78 includes a pair of contacts 118, 120 which are normally open with the footplate 72 in the horizontal position. The contact 118 is connected to conductor 88 to control operation of the solenoid 90. The contact 120 is connected through a conductor 122 to a solenoid 124 of a supply valve 126 that is biased to a first position by a spring 128. In the first position, the inlet port 130 of valve 126 is disconnected from the outlet port 132 that is in turn connected to the inlet 96 of valve 92. The solenoid 124 operates to move the valve 126 against the bias of spring 128 to connect the inlet 130 with the outlet port 132.

The inlet 130 is connected through a pressure regulator 134 to a reservoir 136 so that air from the reservoir is supplied at constant pressure to the inlet port 130.

The conductor 122 is also connected to one input of an AND gate 140 that receives as its other input the output of the mercury switch 50 on the probe unit 12. An L.E.D. 139 is connected in the circuit from the switch to the AND gate 140 to provide a visual indication of the correct attitude of the body 44. The AND gate 140 controls the transfer of data from a latch 142 within a microprocessor 144 to a register 146. The latch receives data from the data output 70 of the drive unit 14 through a data bus 148. The register 146 is connected to a second latch 150 that is in turn connected to a RAM 152. The transfer of contents between the latch 150 and RAM 152 is controlled by an enable signal generated by a CPU 156 and conveyed to the second latch 150 by a data bus 154 that is also connected to the register 146.

The operation of the device will now be described assuming that the probe is in a retracted position and the foot pedal maintained under the influence of the spring 75 in a horizontal position. Under the conditions the valves 92, 106 and 126 are in the positions indicated so that flow of fluid (air) from the reservoir 136 is prevented by supply valve 128 and the evacuation of the supply port 68 by the pump 116 is prevented by retraction valve 106. The supply port 68 is, however, vented by the vent valve 92 so that the piston 62 and the drive unit 14 is held by counterbalancing spring 66 in its fully retracted position. In this situation the inner cable 36 is fully withdrawn within the bore 46 so that the tip of the probe 37 is flush with the planar endface 52. Any slight adjustment to ensure that the tip of the probe 37 is flush with the endface 52 is provided by an adjustment of the outer sheath 32 relative to the sleeve 26 by releasing the thumbscrews 34 and repositioning the sheath.

The probe unit 12 is then inserted into the patient's mouth and positioned with the planar end surface 32 on the incisal or occulusal edge of the tooth being investigated. With probe body 12 in the desired position the inner cable 36 is advanced by depressing the footplate 72 clockwise about the fulcrum 74 so that the contacts 118 and 120 are closed. The closing of the contact 118 causes the valve 92 to move to a position in which the vent port 100 is closed and the inlet 96 is connected to the outlet 98. Similarly, closing the contact 120 energizes the solenoid 124 and causes the valve 126 to move to a position in which the inlet 130 is connected to the outlet 132. Air under a controlled pressure from the regulator 134 is thus supplied to the supply port 68 and acts on the piston 62 to move it against the counterbalancing spring 66 and move the piston rod 22 along the sleeve 26. This motion is transmitted through the connector 40 to the cable 36 so that the opposite end of the cable 36, namely the probe 37, extends beyond the planar end surface 52. The cable will extend until it meets a resistance equivalent to the force exerted on the piston 62. Because the pressure applied to the pistons 62 is maintained constant by the regulator 134, the force required to stop movement of the inner cable 36 will be constant over different measurements.

Closing of the contact 120 also provides a signal to the AND gate 140 and provided the body 44 is held in a predetermined orientation a signal will also be provided by the mercury switch 50. The output of the AND gate 140 thus enables the latch 142 to transfer data from the data port 70 that indicates the movement of the pistons 62 along the cylinder 64 and thus the advance of the inner cable 36 beyond the endface 52 into the register 146. The contents of the register 146 are continuously sampled by the CPU 156 until a stable reading is achieved indicating that movement of the inner cable 36 has stopped. Once this occurs the CPU 156 enables the latch 150 to transfer the data into a RAM 152 to provide an indication of the distance from the incisal edge of the tooth to the tip of the probe 37.

Once the data has been entered, the cable 36 is retracted by moving the footplate 72 in a counterclockwise direction to open the contacts 118, 120 and close the contacts 84, 86 at switch 76. Once the contact 120 of switch 78 is open, the solenoid 124 is de-energised and the valve 126 moves back under the influence of the spring 128 to a position in which flow from inlet 130 to outlet 132 is prevented. The closing of contact 84 of switch 76, however, maintains the vent valve 92 in a non-venting position and the closing of contact 86 causes the solenoid 104 of valve 106 to move to a position in which the inlet 110 is connected to the outlet 112. The pump 116 is then effective to evacuate the supply port 68 and cause the pistons 62 to retract within the cylinder 64 and withdraw the inner cable 36. During this movement, the input to AND gate 140 is interrupted and so contents from the latch 142 are not transferred into the register 146.

Once the inner cable 36 is fully retracted, release of the foot pedal 72 causes the vacuum valve 106 to move under the influence of spring 108 to disconnect the vacuum pump 116 from the supply port 68 and allow the vent valve 92 to move to a venting position.

The probe may be used in a number of ways to collect data. In order to determine the pocket depth adjacent a tooth, the probe 12 is inserted in the mouth and located against the incisal edge as indicated able. The cable 36 is initially advanced along the edge of the tooth within the pocket between the gum and the tooth. Once advance of the probe terminates, a direct measurement of the distance of the attachment point to the incisal or occlusal edge is stored in the microprocessor.

In order to obtain the depth of the pocket, the probe can initially be advanced until it abuts the gingival margin and this measurement is stored in the RAM. The probe is then retracted and advanced into the pocket until it reaches the bottom of the pocket. Again this data is transferred into the RAM and the depth of the pocket obtained by subtracting the one reading from the other.

Similarly, these tests can be repeated at different intervals during the treatment of a patient and the progress or success of the treatment determined.

Because the probe is always advanced with a constant force, the repeatability of readings is good so that relative measurements over a period of time provide an accurate indication of the effectiveness of treatment or the advance of the gum disease. Moreover, the provision of the attitude sensing switch 50 enhances the accuracy of the data and the repeatability of the results. It will be noted that the attitude sensor 50 operates to inhibit operation of the data collection rather than operation of the probe so that the probe may still be advanced even if the attitude of it varies slightly during the advance. However, the data will not be transferred unless the probe is accurately aligned.

It will of course be appreciated that modifications can be made within the scope of the present invention. For example, the retraction of the piston 62 could be accomplished by directing pressurized fluid to the opposite side of the piston 62 to produce a pressure differential to retract the probe. Alternatively, a stepping motor could be provided to advance the probe with suitable force regulating circuits.

The data obtained may be manipulated in a number of ways, for example to obtain velocity profiles of the probe tip penetration into the gingival tissue indicative of the relative tightness of attachment of the tissue to the tooth. The ability of the probe unit 12 to use the incisal edge of the tooth as a datam facilitates rapid measurement and avoids the need for stents and the like.

What we claim is:

1. Apparatus for determining the attachment point of tissue to a tooth comprising:
   a body for insertion into the mouth;
   a datum surface on said body for engagement with a location on the tooth;
   a probe moveable relative to said datum surface into engagement with said tissue;
   drive means operable upon said probe to control movement thereof;
   measuring means to measure movement of said probe relative to said datum surface, said drive means including force control means to regulate the force applied by said drive means to said probe to maintain said force at a predetermined value; and
   attitude sensing means located on said body for inhibiting operation of said measuring means upon movement of said body from a predetermined attitude, thereby permitting movement of said probe when said body is positioned in any attitude whilst inhibiting the measuring of such movement of said probe until said body is positioned in said predetermined attitude while allowing the measuring of movement once said body is positioned in said predetermined attitude.

2. Apparatus according to claim 1 wherein said drive means is remote from said body.

3. Apparatus according to claim 2 wherein said drive means includes a reciprocable fluid motor and a source of pressurized fluid.

4. Apparatus according to claim 3 wherein said drive means is connected to said body by a flexible sheath and to said probe by an inextensible member slidable within said sheath.

5. Apparatus according to claim 4 wherein said force control means includes pressure regulating means to regulate the pressure of fluid supplied from said source to said fluid motor.

6. Apparatus according to claim 5 wherein said drive means includes a manually operable control to control supply of fluid to said motor.

7. Apparatus according to claim 6 wherein said manually operable control is operative in a first position to provide a pressure differential across said motor in a direction to advance said probe and in a second position to provide a pressure differential across said motor in a direction to retract said probe.

8. Apparatus according to claim 7 wherein said control is operative in a third position to minimize the pressure differential across said motor.

9. Apparatus according to claim 7 wherein said measuring means are inhibited upon movement of said control from said first position.

10. Apparatus according to claim 5 wherein said force control means includes first valve means to control the flow of fluid to said motor and a manual controller operable upon said valve means.

11. Apparatus according to claim 10 wherein said drive means includes a source of low pressure fluid and said force control means includes second valve means to connect said motor to said source of low pressure fluid.

12. Apparatus according to claim 11 wherein said force control means includes third valve means providing a vent for said motor.

13. Apparatus according to claim 12 wherein said controller is operable upon each of said valve means to condition said first valve means to supply fluid when said second and third valve means are conditioned to disconnect said motor from said low pressure source and said vent respectively.

14. Apparatus according to claim 13 wherein said controller is operable to condition said second valve means to connect said motor to said low pressure source when said first and third valve means are conditioned to disconnect said motor from said pressurized source and said vent respectively.

15. Apparatus according to claim 14 wherein said controller is operable to condition said third valve to vent said motor when said first and second valve means are conditioned to disconnect said motor from said pressurized and low pressure source respectively.

16. Apparatus according to claim 1 wherein control means are provided to control operation of said drive means and are operative in a first position to advance said probe, said control means being operative to inhibit operation of said measuring means when not in said first position.

17. Apparatus according to claim 16 including data storage means operatively connected to said measuring means.

18. Apparatus according to claim 17 wherein said data storage means including sampling means to sample periodically the output of said measuring means and store data upon said output remaining stable.

19. Apparatus according to claim 17 wherein transfer of data from said measuring means to said storage means is inhibited by said attitude sensing means.

20. Apparatus according to claim 19 wherein transfer of data from said measuring means to said data storage means is inhibited by movement of said control means from said first position.

21. A method of determining the attachment point of tissue to a tooth comprising the steps of:
providing a body for insertion into a mouth, said body having a datum surface for engagement with a location on said tooth; advancing a probe from said body toward said tissue by applying a constant force to said probe; determining a location of the leading edge of said probe relative to said datum surface upon said probe engaging said tissue and being arrested thereby; and
preventing the measurement of said location until said body is positioned in a predetermined attitude while allowing said measurement once said body is in said predetermined attitude.

* * * * *